(12) United States Patent  
Sato

(10) Patent No.: US 12,076,104 B2  
(45) Date of Patent: Sep. 3, 2024

(54) MEDICAL TOOL FOR FINGERTIP

(71) Applicant: NATIONAL UNIVERSITY CORPORATION KOCHI UNIVERSITY, Kochi (JP)

(72) Inventor: Takayuki Sato, Kochi (JP)

(73) Assignee: NATIONAL UNIVERSITY CORPORATION KOCHI UNIVERSITY, Kochi (JP)

( * ) Notice: Subject to any disclaimer, the term of this patent is extended or adjusted under 35 U.S.C. 154(b) by 596 days.

(21) Appl. No.: 17/421,457

(22) PCT Filed: Jun. 30, 2020

(86) PCT No.: PCT/JP2020/025643  
§ 371 (c)(1),  
(2) Date: Jul. 8, 2021

(87) PCT Pub. No.: WO2021/006113  
PCT Pub. Date: Jan. 14, 2021

(65) Prior Publication Data  
US 2022/0079697 A1 Mar. 17, 2022

(30) Foreign Application Priority Data  
Jul. 9, 2019 (JP) .................................. 2019-127358

(51) Int. Cl.  
*A61B 42/20* (2016.01)  
*A41D 19/00* (2006.01)  
(Continued)

(52) U.S. Cl.  
CPC .......... *A61B 42/20* (2016.02); *A41D 19/0157* (2013.01); *A61B 5/0071* (2013.01);  
(Continued)

(58) Field of Classification Search  
CPC ..... A61B 42/20; A61B 5/0071; A61B 5/0084; A61B 5/6826; A61B 90/30; A61B 90/36;  
(Continued)

(56) References Cited

FOREIGN PATENT DOCUMENTS

JP 2002-291746 A 10/2002  
JP 2008-038306 A 2/2008  
(Continued)

OTHER PUBLICATIONS

Sep. 13, 2022 Office Action issued in Japanese Patent Application No. 2021-530623.

(Continued)

*Primary Examiner* — Mark W. Bockelman  
(74) *Attorney, Agent, or Firm* — Oliff PLC

(57) ABSTRACT

A medical tool for fingertip of the present invention has a resin layer that emits red fluorescence or near-infrared fluorescence, and is used by putting it on a fingertip. More specifically, the medical tools for fingertip 1A to 1E have a finger cot shape and an opening portion 2 from which the ball of the finger is exposed when put on, and are formed of a resin that emits red fluorescence or near-infrared fluorescence. Alternatively, the medical tools for fingertip 1F and 1G have a glove shape, and a printing layer 8, 9 that is formed of a resin that emits red fluorescence or near-infrared fluorescence on or around the ball of the finger thereof. Further alternatively, the medical tools for fingertip 1H and 1I are a sticker-like medical tool having an adhesive layer provided to one surface of the resin layer that emits red fluorescence or near-infrared fluorescence, and have a size that allows it to be attached to the ball of the finger. When the medical tools for fingertip are put on the tip of a finger of a surgeon used for palpation of a living body, the position (Continued)

of an affected site which has been specified from the mucosal side by the palpation can be accurately specified from the serosal side.

11 Claims, 11 Drawing Sheets

(51) Int. Cl.
  *A41D 19/015* (2006.01)
  *A61B 5/00* (2006.01)
  *A61B 90/00* (2016.01)
  *A61B 90/30* (2016.01)
(52) U.S. Cl.
  CPC .......... *A61B 5/0084* (2013.01); *A61B 5/6826* (2013.01); *A61B 90/30* (2016.02); *A61B 90/36* (2016.02); *A41D 19/0013* (2013.01); *A41D 19/0027* (2013.01); *A41D 19/0055* (2013.01); *A61B 2090/304* (2016.02)
(58) Field of Classification Search
  CPC ............ A61B 2090/304; A61B 5/0086; A61B 5/4255; A61B 2017/00438; A61B 2090/309; A61B 42/10; A61B 90/00; A41D 19/0157; A41D 19/0013; A41D 19/0027; A41D 19/0055
  See application file for complete search history.

(56) References Cited

FOREIGN PATENT DOCUMENTS

| | | | |
|---|---|---|---|
| JP | 2011-162445 | A | 8/2011 |
| JP | 2015-126885 | A | 7/2015 |
| JP | 2016-192997 | A | 11/2016 |
| JP | 2017-104147 | A | 6/2017 |
| JP | 6161096 | B2 | 7/2017 |
| JP | 6675662 | B1 | 4/2020 |
| WO | 2016/132596 | A1 | 8/2016 |
| WO | 2017/208596 | A1 | 12/2017 |
| WO | 2018/123300 | A1 | 7/2018 |

OTHER PUBLICATIONS

Jan. 24, 2023 Office Action issued in Japanese Patent Application No. 2021-530623.
May 1, 2023 Office Action issued in Japanese Patent Application No. 2021-530623.
Aug. 25, 2020 International Search Report issued in Patent Application No. PCT/JP2020/025643.
Sep. 4, 2020 Reconsideration Report by Examiner before Appeal issued in Japanese Patent Application No. 2020-007001.
May 19, 2020 Office Action issued in Japanese Patent Application No. 2020-007001.
Mar. 3, 2020 Office Action issued in Japanese Patent Application No. 2020-007001.
Jan. 7, 2020 Office Action issued in Japanese Patent Application No. 2019-127358.
Oct. 23, 2019 Office Action issued in Japanese Patent Application No. 2019-127358.
Jan. 11, 2022 International Preliminary Report on Patentability issued in Patent Application No. PCT/JP2020/025643.

MEDICAL TOOL FOR FINGERTIP

TECHNICAL FIELD

The present invention relates to a medical tool for fingertip including a resin layer that emits red or near-infrared fluorescence and is put on a fingertip.

BACKGROUND ART

An endoscope is used to diagnose cancer or the like developed in the mucosa of a human tubular tissue such as the rectum. The diagnosis is performed in combination with palpation in which a finger of the surgeon is inserted into the body. Regarding this, a finger cot, provided with an opening portion for palpation on the tip and with an image-capturing device attached to the tip, has been proposed (Patent Literature 1).

CITATION LIST

Patent Literature

Patent Literature 1: Japanese Patent Application Laid-Open No. 2002-291746

SUMMARY OF INVENTION

Technical Problem

The finger cot described in Patent Literature 1 is put on a finger, then the finger is inserted into a human tubular tissue such as the rectum. This makes it possible to observe the surface state of the human tubular tissue on the mucosal side and perform palpation of the tissue on the mucosal side. Further, in a case where a resection treatment of cancer is required, a puncture treatment can be performed while the affected site is being observed.

On the other hand, surgical resection of cancer developed in the mucosa of the human tubular tissue requires the position of the cancer to be specified from the serosal side of the human tubular tissue. However, the position of the cancer cannot be specified from the serosal side by using the finger cot described in Patent Literature 1. Thus, for example, in a case where rectal cancer is diagnosed by an endoscope or palpation, the resection is generally performed with a margin range of about 2 cm around the position of the diagnosed cancer. Having such a margin range sometimes results in the removal of the sections of the anus where the presence of cancer is not confirmed, leading to the necessity for an artificial anus.

Regarding the abovementioned problems, an object of the present invention is to specify, if a medical doctor specifies a position of an affected site by performing palpation of the mucosa of a human tubular tissue such as the rectum, the position of the affected site from the serosal side of the human tubular tissue.

Solution to Problem

The present inventor has conceived that, when a resin layer that emits red fluorescence or near-infrared fluorescence is put on the tip of a finger used for palpation, the position of an affected site which has been specified from the mucosal side by the palpation can be specified from the serosal side by observing the fluorescence emitted by the resin layer from the serosal side, thereby completing the present invention.

That is, the present invention provides a medical tool for fingertip, which is used by putting it on a fingertip, having a resin layer that emits red fluorescence or near-infrared fluorescence.

Advantageous Effects of Invention

According to the present invention, the resin layer that emits red fluorescence or near-infrared fluorescence can be put on a fingertip, making it possible to specify the position of the affected site from the serosal side, which has been specified by the palpation from the mucosal side, by observing the fluorescence emitted by the resin layer. Thus, when the affected site specified by the palpation from the mucosal side is surgically resected, the margin of the resection range required due to not being able to accurately specify the position of the affected site can be significantly reduced or eliminated, thereby minimizing the resection range. As a result, a section of the anus, which would have been unnecessarily removed before, can be conserved, for example, reducing the burden of the patient.

Further, palpation can be performed according to the present invention, and thus the size of the cancer or the like can be accurately diagnosed on the basis of the hardness of the mucosa.

DESCRIPTION OF EMBODIMENTS

Hereinafter, the present invention will be described in detail with reference to drawings. Note that, in each of the drawings, the same reference symbols indicate the same or equivalent constituent elements.
(Medical Tool for Fingertip with Finger Cot Shape)

Figure 1:
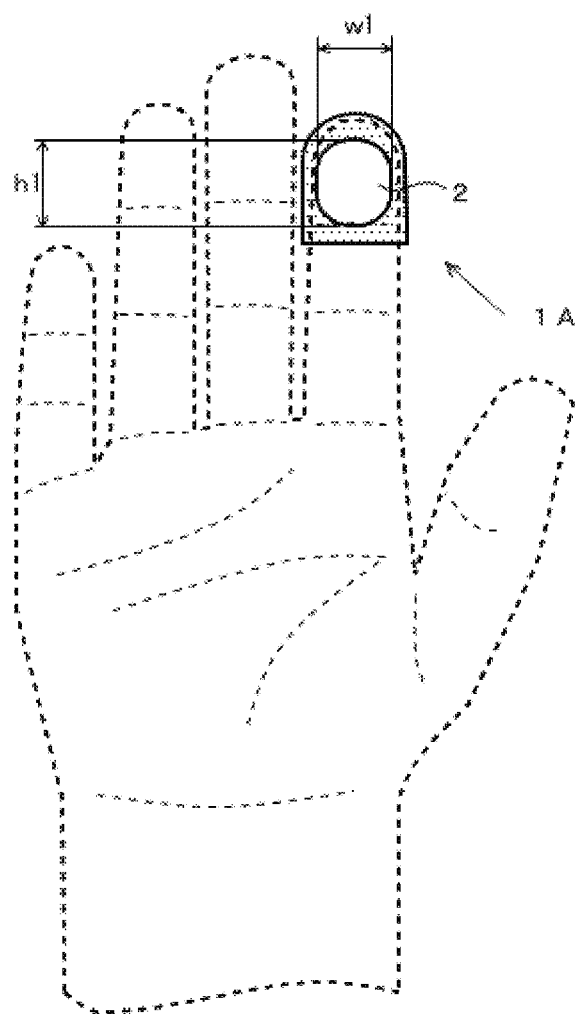
FIG. 1 is an elevation view of a medical tool for fingertip 1A of Example having a finger cot shape.

FIG. 1 is an elevation view of a medical tool for fingertip 1A of one example of the present invention with a finger cot shape. In FIG. 1, a broken line indicates a hand having the medical tool for fingertip 1A with a finger cot shape put on a finger. As shown, the medical tool for fingertip of the present invention is configured such that a resin layer that emits red fluorescence or near-infrared fluorescence is put on a fingertip, in particular, on the ball of a finger or around the ball of a finger. More specifically, the medical tool for fingertip 1A has a length to cover the finger from the fingertip to the first joint of the finger when put on and includes an opening portion 2 from which at least a center portion of the ball of the finger is exposed. Including the opening portion 2 allows a surgeon to easily perform palpation using the ball of the finger exposed from the opening portion 2.

As of the size of the opening portion 2, a width w1 is preferably set to 5 to 15 mm and a length h1 is preferably set to 5 to 20 mm from the standpoint of allowing palpation. On the other hand, as described below, when the opening portion of the medical tool for fingertip 1A is placed on an affected site of the human tissue on the mucosal side and then the excitation light is applied to the affected site, the resin layer of the medical tool for fingertip 1A emits fluorescence. When such a fluorescent image is observed from the serosal side, the opening portion 2 is observed as being dark and the periphery of the opening portion 2 is observed as being bright in a ring shape, making it possible to specify the position of the opening portion, that is, the position of the affected site. Thus, from the standpoint of specifying the position of the affected site more accurately, the width w1 of the opening portion 2 is preferably set to 10 to 15 mm and the length h1 of the opening portion 2 is preferably set to 10 to 20 mm. On the other hand, if the size of the opening portion 2 is too small, the light-emitting part observed from the serosal side fails to form a ring shape and the part corresponding to the opening portion 2 looks as if it is emitting light, making it difficult to accurately specify the position of the affected site. Conversely, if the size is too large, it becomes difficult to specify which part of the area observed as being dark is the affected site.
(Resin Forming Medical Tool for Fingertip)

The medical tool for fingertip 1A has a resin layer that is formed of a resin that emits red fluorescence or near-infrared fluorescence. As the resin that emits red fluorescence or near-infrared fluorescence, for example, a flexible resin in which a fluorescence dye is kneaded can be used. As the flexible resin described herein, polyurethane, polypropylene, polyethylene, polyvinyl chloride, polyamide, polyamide elastomer, or the like compounded with a curing agent as necessary, can be used. The resin preferably has the shore hardness of from 30A to 70A after curing. Further, using the resin having the elongation at break of 300% or more causes excellent fit feeling that comes when the medical tool for fingertip 1A having a finger cot shape is put on the fingertip.

The preferable thickness of the resin layer forming a finger cot shape is determined according to the emission intensity of the resin layer containing the fluorescence dye. Thus, the preferable thickness of the resin layer varies according to a type and concentration of the fluorescence dye. However, normally, the thickness is preferably from 0.1 to 2 mm.
(Fluorescence Dye)

The fluorescence dye kneaded in the flexible resin preferably emits fluorescence in a red-to-near-infrared wavelength region of from 600 to 1400 nm, preferably in a red or near-infrared light wavelength region of from 700 to 1100 nm. Light of such a wavelength region has a high transmittance into human tissues such as skin, fat, and muscle, and, for example, it can satisfactorily reach from the mucosa to the serosal surface of the human tubular tissue such as the rectum.

Examples of the fluorescence dye that emits the fluorescence in the abovementioned wavelength region may include riboflavin, thiamine, nicotinamide adenine dinucleotide (NADH), indocyanine green (ICG), azo-boron complexes compound described in Japanese Patent Application Laid-Open No. 2011-162445, and dyes containing a condensed ring structure described in WO2016/132596.

A preferable concentration of the fluorescence dye in the resin that emits near-infrared fluorescence is determined according to a type and the like of the fluorescence dye and the resin as a binder. Normally, the concentration is preferably determined in a range of from 0.001 to 1% by mass.

Examples of a method of incorporating the fluorescence dye in the flexible resin may include a method in which the fluorescence dye is kneaded in the resin by using a biaxial kneader. Then, the kneaded product is molded into a finger cot shape by extrusion molding or injection molding.
(Additives)

A contrast agent such as barium sulfate may be added to the fluorescent resin as needed. In this case, even if the medical tool for fingertip 1A comes off from the finger in the living body, the medical tool for fingertip 1A can be tracked in the living body by using X-ray photography.
(Using Method of Medical Tool for Fingertip)

Figure 2A:
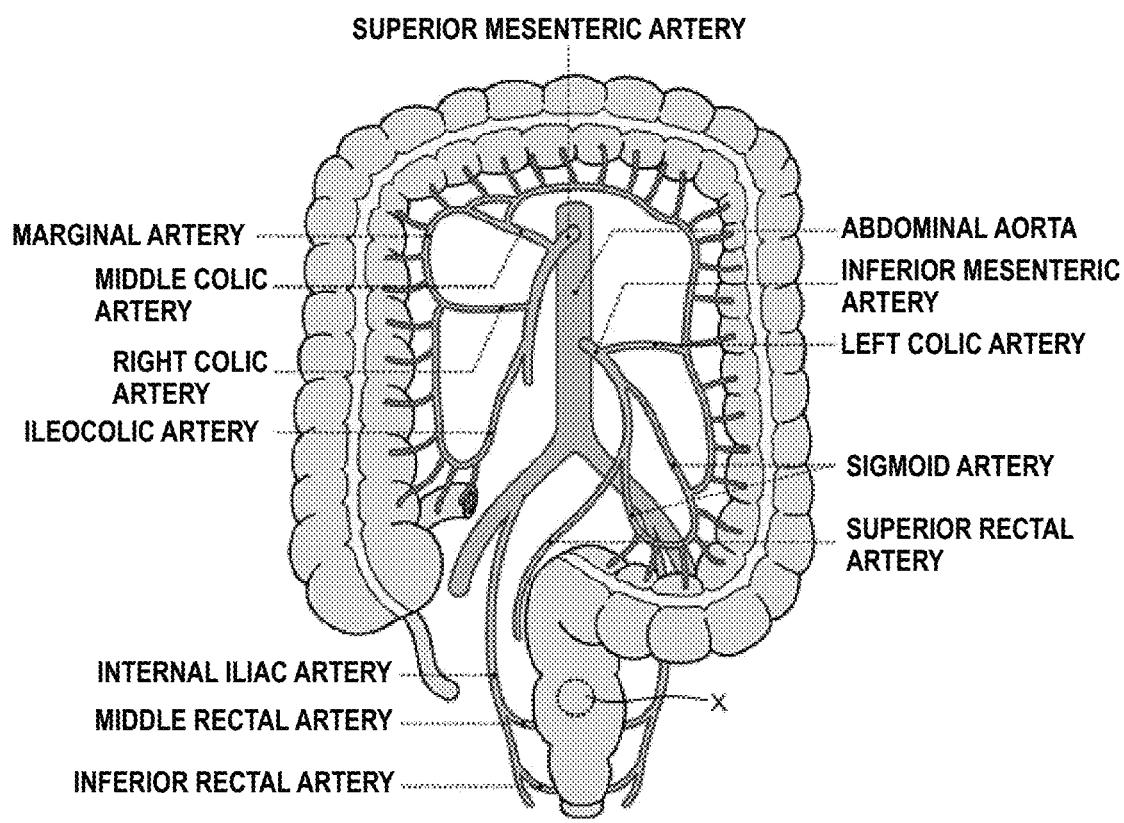
FIG. 2A is an explanatory view of a position of an affected site in the body in a case where the affected site is in the rectum.

A method of using the medical tool for fingertip 1A involves, first, putting the medical tool for fingertip 1A having a finger cot shape on a finger of a surgeon's hand, preferably a surgeon's hand wearing a surgical glove as illustrated in FIG. 1, in order to specify a position X of the rectal cancer illustrated in FIG. 2A from the serosal side, for example. In this case, the opening portion 2 is placed on the ball of the finger.

Figure 2B:
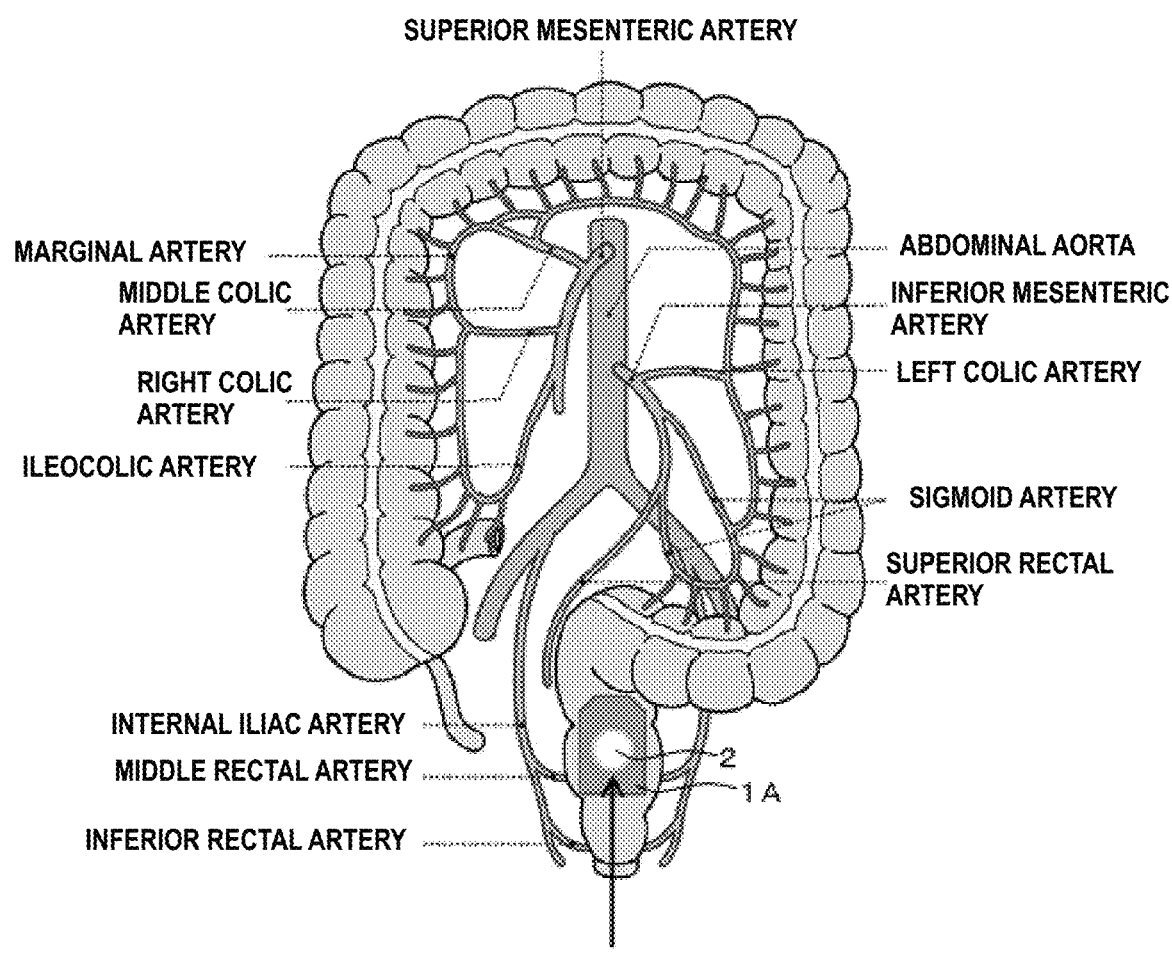
FIG. 2B is an explanatory view of a method for specifying the position of the affected site in the rectum by the medical tool for fingertip 1A of Example.

Next, as illustrated in FIG. 2B, the finger wearing the medical tool for fingertip 1A having a finger cot shape is inserted in the rectum from the anus to perform palpation of the rectum, thereby specifying the position of the cancer. The cancer is pressed down by the ball of the finger exposed from the opening portion 2. Then, excitation light for causing emission of red fluorescence or near-infrared fluorescence is applied to the resin forming the medical tool for fingertip 1A from the serosal side of the rectum, and the fluorescence emitted from the medical tool for fingertip 1A is observed from the serosal side.

In this operation, an irradiation method of the excitation light may involve irradiating the serosa of the rectum, which has been exposed by the abdominal surgery, with the excitation light or irradiating the site from the serosal side after a surgical endoscope is inserted from an incision made in the wall of the abdomen. The wavelength of the excitation light is shorter than that of the fluorescence. However, the wavelength region of the excitation light causing emission of red fluorescence or near-infrared fluorescence also has a high transmittance through human tissue. Thus, the excitation light applied from the serosal side is absorbed by the medical tool for fingertip 1A on the mucosal side with it barely being absorbed by or interfered by the tissue of the rectum or the blood, thereby causing the resin layer of the medical tool for fingertip 1A to emit red fluorescence or near-infrared fluorescence. As a result, the ring shape emission from the medical tool for fingertip 1A can be easily observed from the serosal side, in a case of red fluorescence, by naked eyes, and, in a case of near-infrared fluorescence, through a known infrared-to-visible light conversion glass or by imaging the rectum from the serosal side and visualizing the near-infrared fluorescence by image processing. Further, the dark part caused by the opening portion 2 inside the ring-shaped emission part can be specified as the position of the developing cancer. When the position of the cancer can be specified from the serosal side in this manner, the position of the cancer is marked by an electric scalpel, so that such a mark can be used as a guide during resection of the affected site.

A situation where the medical tool for fingertip 1A of the present invention is applied is not limited to the case where the position of the affected site to be specified is within a range where the finger inserted from the outside of the human body can reach as described above with the rectum. For example, it can be used in a case where the finger wearing the medical tool for fingertip 1A is inserted in an incision made in the wall of the abdomen for inserting a laparoscope and a surgical instrument and then further inserted in the gastric cavity from an incision made in the stomach wall to specify the position of the affected site in the gastric mucosa from the gastric serosal side.

Note that, for example, when a metal clip described in Japanese Patent No. 6161096 is used to pinch the mucosa of the affected site, the position of the affected site can be specified by observing the affected site from the serosal side using the emission of the fluorescence dye-containing resin attached to the clip. However, scalpels may be damaged by colliding with the metal clip during the resection of the affected site. In contrast, according to the medical tool for fingertip of the present invention, even if the medical tool for fingertip comes off the finger of the surgeon in the living body and the scalpel collides with the medical tool for fingertip during the resection of the affected site, no damage is caused to the scalpel.

(Modified Embodiment of Medical Tool for Fingertip)

Figure 3:
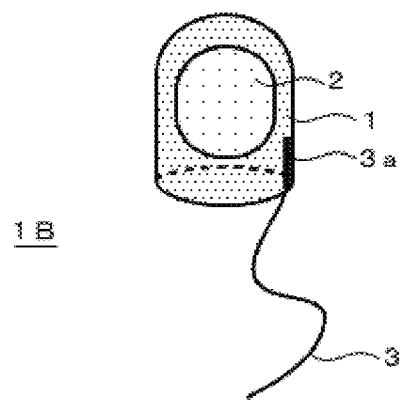
FIG. 3 is a perspective view of a medical tool for fingertip 1B of Example.

The medical tool for fingertip of the present invention can be provided in various embodiments. For example, a medical tool for fingertip 1B illustrated in FIG. 3 is obtained by attaching a pull string 3 to an end portion of the medical tool for fingertip 1A illustrated in FIG. 1 by adhesion or welding. Even if the medical tool for fingertip 1B attached with the pull string 3 comes off from the fingertip in the body, the medical tool for fingertip 1B can be easily taken out from the body by pinching and pulling the pull string 3.

Note that, in order to firmly attach the pull string 3 to a medical tool main body for fingertip 1, it is preferable to maintain a sufficient length of an attachment region 3a of the pull string 3.

Figure 4:
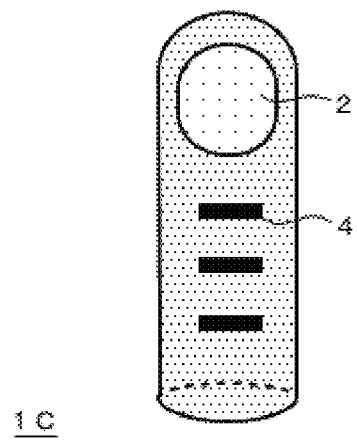
FIG. 4 is a perspective view of a medical tool for fingertip 1C of Example.

A medical tool for fingertip 1C illustrated in FIG. 4 is configured in such a manner that the length of the medical tool for fingertip 1A illustrated in FIG. 1 is extended, so that it covers the finger from the fingertip to the second joint, and scales 4 are provided at prescribed intervals on the lower side from the opening portion 2 (that is, a finger insertion side) using a red or near-infrared light nontransmitting resin. In this configuration, when the medical tool for fingertip 1C on the mucosal side is observed from the serosal side, the opening portion 2 and the scales 4 are observed as dark areas in the light-emitting region with a finger cot shape, making it possible to use the scales as a guide for determining an resection margin of the affected site.

Figure 5:
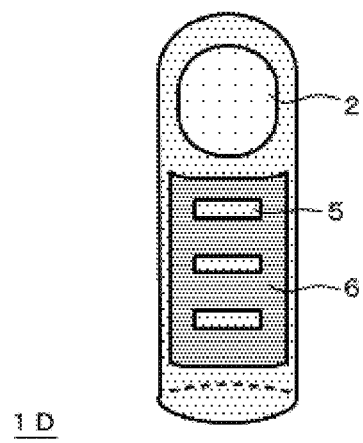
FIG. 5 is a perspective view of a medical tool for fingertip 1D of Example.

A medical tool for fingertip 1D illustrated in FIG. 5 is configured in such a manner that, instead of forming the scales using the red or near-infrared light nontransmitting resin in the medical tool for fingertip 1C illustrated in FIG. 4, a red or near-infrared light nontransmitting resin layer is provided by attaching a red or near-infrared light nontransmitting resin film 6, including holes 5 punched out in a shape of scales, to the medical tool main body 1, printing the red or near-infrared light nontransmitting resin layer on the medical tool main body 1, or the like. The resin that emits red or near-infrared fluorescence is exposed from the holes 5, thus, when the excitation light is applied and the medical tool for fingertip 1D is observed from the serosal side, the opening portion 2 is observed as a dark area in the light-emitting region with a finger cot shape on the fingertip side of the medical tool for fingertip 1D put on the finger, while the scales emitting light in the dark region can be observed on the lower side of the opening portion.

Figure 6:
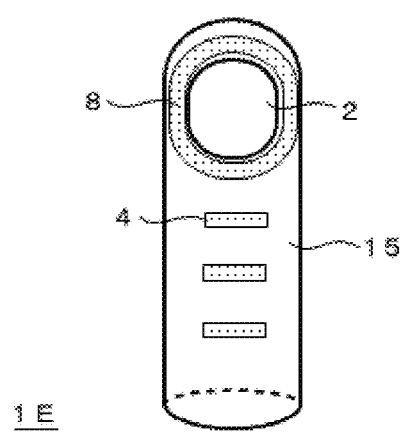
FIG. 6 is a perspective view of a medical tool for fingertip 1E of Example.

A medical tool for fingertip 1E illustrated in FIG. 6, like the medical tool for fingertip 1C illustrated in FIG. 4, has a shape of the finger cot including the opening portion 2 and has a length to cover the finger from the fingertip to the second joint. However, the shape of the finger cot itself is formed by a resin 15 without the fluorescence dye that emits red fluorescence or near-infrared fluorescence. On the other hand, a resin layer 8 having a ring shape is formed around the opening portion 2 by applying a coating material containing the fluorescence dye that emits red fluorescence or near-infrared fluorescence. Further, the scales 4 are formed on the lower side of the opening portion 2 by the coating material containing the fluorescence dye that emits red fluorescence or near-infrared fluorescence. This medical tool for fingertip 1E can be used in the same manner as the medical tool for fingertip 1C illustrated in FIG. 4.

In a case where the medical tool for fingertip of the present invention is formed in the finger cot shape having the opening portion as described above, as an aspect of forming a medical tool for fingertip using a resin that emits red fluorescence or near-infrared fluorescence, it only requires that at least the periphery of the opening portion be formed by the resin that emits red fluorescence or near-infrared fluorescence. Thus, the entire finger cot shape may be formed by such a resin as in the medical tool for fingertip 1A illustrated in FIG. 1. Alternatively, the resin layer 8 that emits red fluorescence or near-infrared fluorescence may be formed around the opening portion 2 as a coating layer as in the medical tool for fingertip 1E illustrated in FIG. 6.

Figure 7:
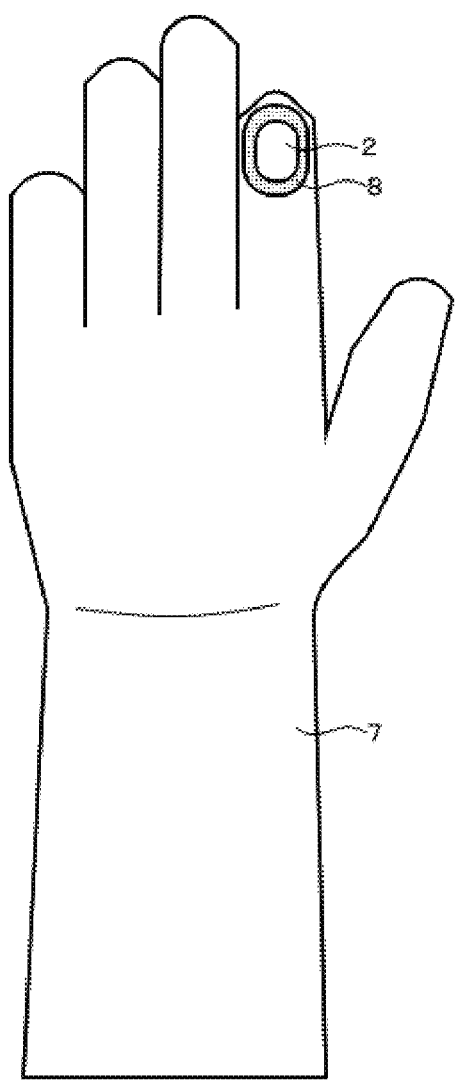
FIG. 7 is a perspective view of a medical tool for fingertip 1F of Example.

A medical tool for fingertip 1F illustrated in FIG. 7 has a glove shape and this glove 7 includes a printing layer 8 having a ring shape formed by a resin that emits red or near-infrared fluorescence in a part corresponding to the ball of the forefinger. This printing layer 8 having a ring shape is formed so as to surround the center part of the ball of the finger.

As the glove 7, a common surgical glove made of natural rubber or synthetic rubber can be used.

According to this medical tool for fingertip 1F, the position of the affected site is specified by palpation using the fingertip, where the printing layer 8 having a ring shape is placed, of the hand wearing the medical tool for fingertip 1F. Then, the excitation light is applied from the serosal side to cause the printing layer 8 having a ring shape to emit red or near-infrared fluorescence. The fluorescence thus emitted is observed from the serosal side in the same manner as that in the medical tool for fingertip 1A illustrated in FIG. 1, so that the affected site can be accurately specified as a dark part inside the light-emitting part having a ring shape formed by the printing layer 8.

Figure 8:
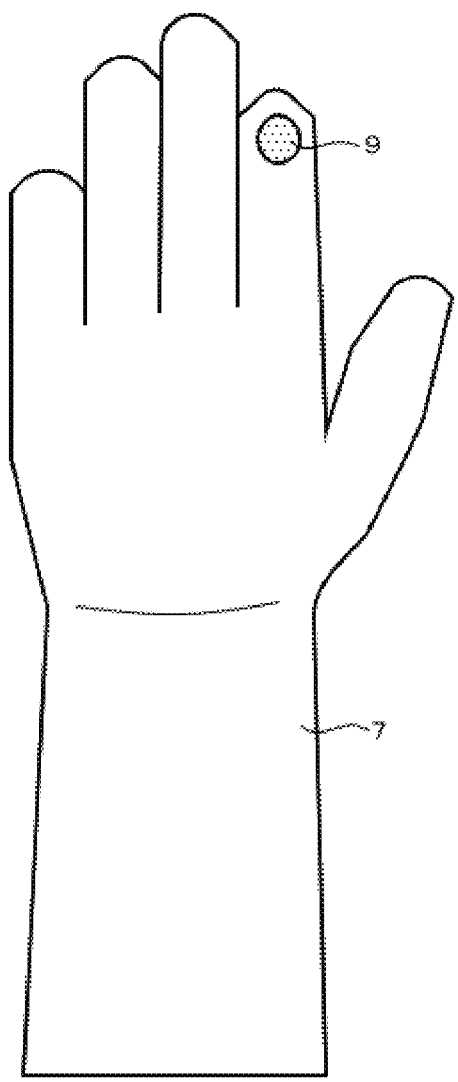
FIG. 8 is a perspective view of a medical tool for fingertip 1G of Example.

A medical tool for fingertip 1G illustrated in FIG. 8 is obtained in such a manner that, instead of including the printing layer 8 having a ring shape formed by the resin that emits red fluorescence or near-infrared fluorescence in the medical tool for fingertip 1F having a glove shape illustrated in FIG. 7, a circular printing layer 9 formed by the same resin is provided. According to this medical tool for fingertip 1G, the affected site can be accurately specified as a circular light-emitting part by observing the fluorescence light-emitting part from the serosal side in the same manner as that in the medical tool for fingertip 1A illustrated in FIG. 1.

Figure 9A:
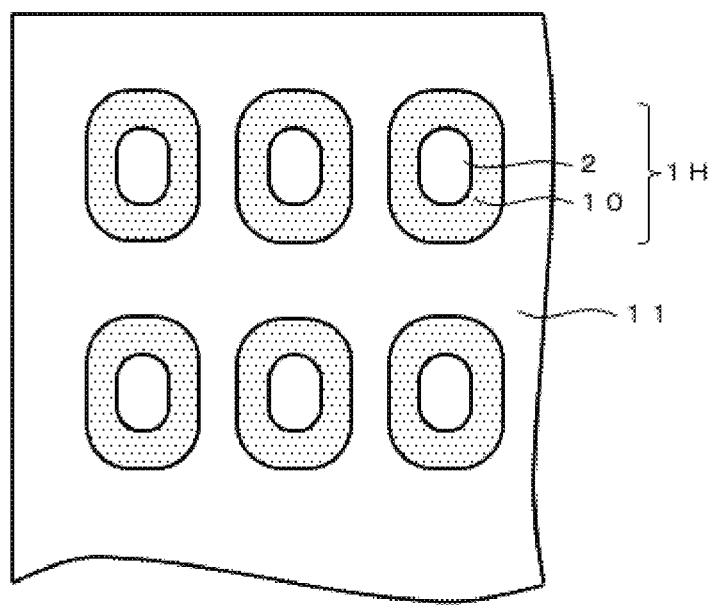
FIG. 9A is a perspective view of a medical tool for fingertip 1H of Example.

A medical tool for fingertip 1H illustrated in FIG. 9A is a sticker-like medical tool for fingertip in which, like the printing layer 8 having a ring shape illustrated in FIG. 7, a resin layer 10 having a ring shape is formed by the resin that emits the red fluorescence or the near-infrared fluorescence, and an adhesive layer is provided to one surface of the resin layer 10 and then attached to a release film 11.

Figure 9B:
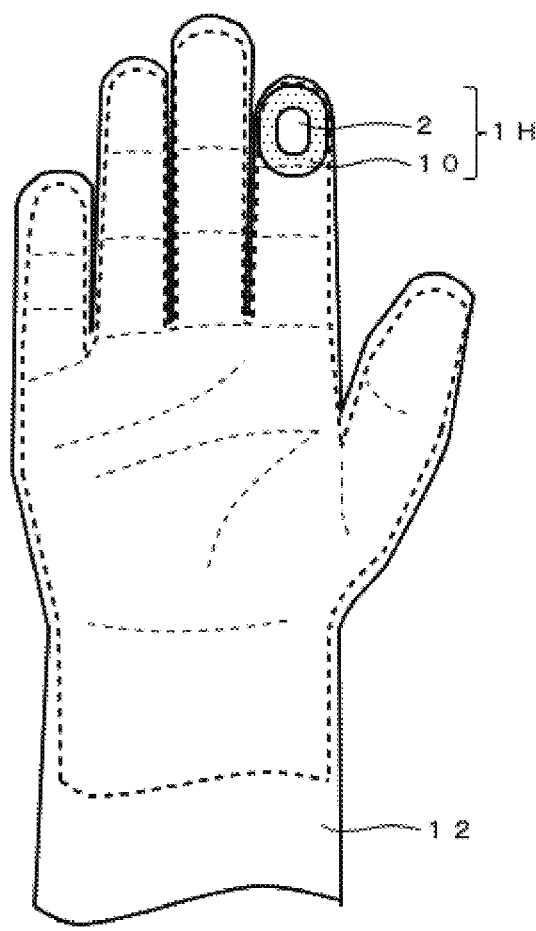
FIG. 9B is a perspective view of the medical tool for fingertip 1H of Example in a state of being attached to a glove.

The resin layer 10 of the sticker-like medical tool for fingertip 1H preferably has a size that allows the resin layer 10 to be attached to the ball of the finger. In this configuration, the medical tool for fingertip 1H is released from the release film 11 and the resin layer 10 having a ring shape is attached to a surgical glove 12 as illustrated in FIG. 9B. This makes it possible to obtain a configuration substantially similar to that of the medical tool for fingertip 1F having a glove shape illustrated in FIG. 7. According to this medical tool for fingertip 1H, the medical tool for fingertip of the present invention can be configured by using the commonly used surgical glove 12 at a lower cost. Further, the method of using the sticker-like medical tool for fingertip 1H may involve directly attaching the resin layer 10 having a ring shape to the ball of the finger and then putting the surgical glove 12 on the finger over the resin layer 10. This can eliminate the risk of the resin layer 10 having a ring shape being peeled off in the body during the palpation.

Figure 10A:
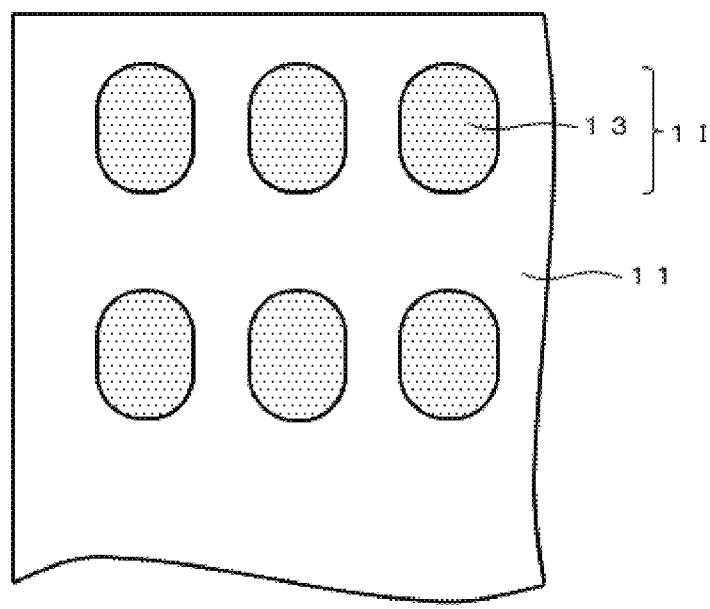
FIG. 10A is a perspective view of a medical tool for fingertip 1I of Example.
Figure 10B:
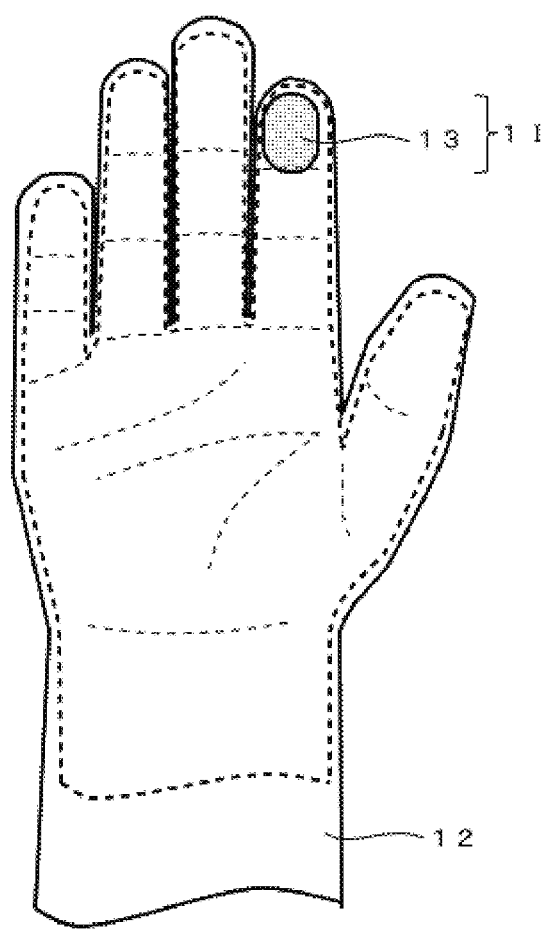
FIG. 10B is a perspective view of the medical tool for fingertip 1I of Example in a state of being attached to a glove.

A medical tool for fingertip 1I illustrated in FIG. 10A is a sticker-like medical tool for fingertip in which the resin layer 10 having a ring shape in the medical tool for fingertip 1H illustrated in FIG. 9A is changed to a circular resin layer 13. This medical tool for fingertip 1I is also released from the release film 11 and the circular resin layer 13 is attached to the surgical glove 12 as illustrated in FIG. 10B. This makes it possible to obtain a configuration substantially similar to that of the medical tool for fingertip 1G having a glove shape illustrated in FIG. 8. A method of using the sticker-like medical tool for fingertip 1I may involve directly attaching the circular resin layer 13 to the ball of the finger and then putting the surgical glove 12 on the finger over the resin layer 13 to eliminate the risk of the circular resin layer 13 being peeled off in the body.

In a case of the sticker-like medical tools for fingertip of the present invention such as the medical tools for fingertip 1H and 1I described above, the resin layers 10 and 13 as a part to be placed on the finger is preferably as thin and flexible as a surgical glove so as not to cause troubles in palpation using the fingertip to which the sticker-like medical tool for fingertip is attached. Thus, it is preferable that the resin layer as a part to be placed on the finger has a thickness of from 0.1 to 0.3 mm, and also has a tensile force at break of 9.0 N or more, an elongation at break of 600% or more, and a tensile force at 300% elongation of 3.0 N or less, similarly to the physical properties of a surgical glove defined by JIS T9107.

The features of the medical tools for fingertip of the present invention described above can be appropriately combined with one another. For example, the medical tools for fingertip 1C and 1D having a finger cot shape illustrated in FIG. 4 and FIG. 5, respectively, may be provided with the pull string 3.

EXAMPLES

Hereinafter, the present invention will be described specifically based on Example.

Figure 11A:
FIG. 11A is an image of the medical tool for fingertip 1A of Example captured under white illumination light using a digital color camera.

A dye containing a condensed ring structure described in WO2016/132596 was kneaded in an ABS resin to produce a medical tool for fingertip 1A having a finger cot shape with a thickness of 2 mm illustrated in FIG. 1. This medical tool for fingertip 1A was put on a finger. FIG. 11A shows an image of the medical tool for fingertip 1A put on the finger captured using white illumination light.

Figure 11B:
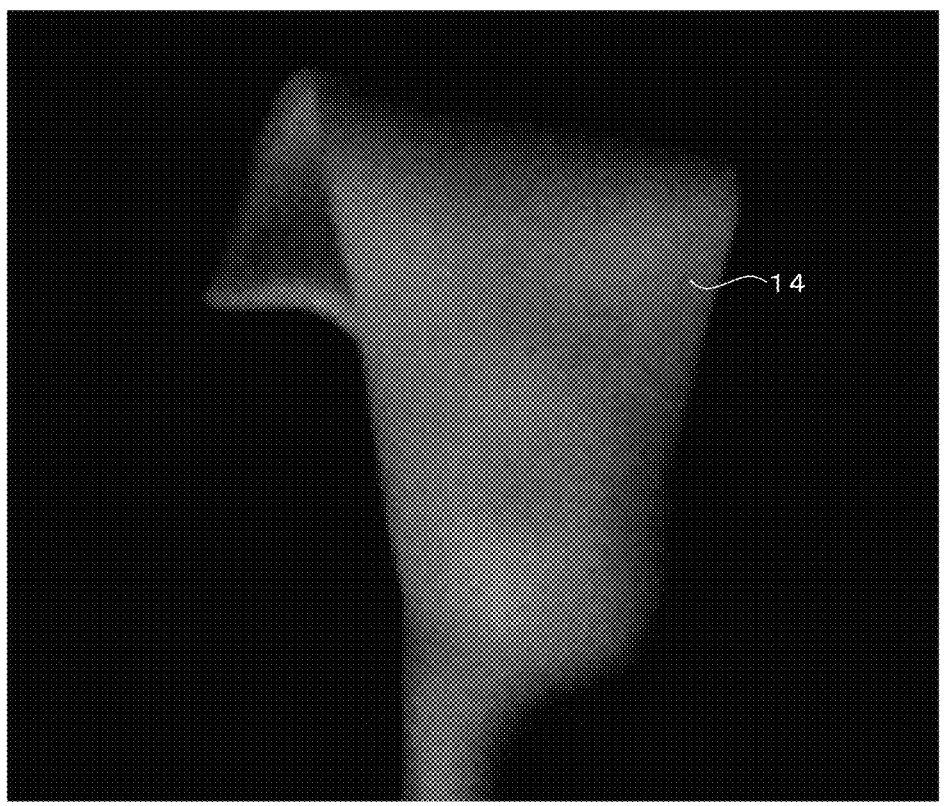
FIG. 11B is an image of a front surface of a silicone sheet behind which the medical tool for fingertip 1A of Example is placed, the image being captured under white illumination light using the digital color camera.

The medical tool for fingertip put on the finger was placed behind a silicone sheet (thickness of 3 mm) 14 imitating a human tissue and an image was captured from the front surface of the silicone sheet 14 under the white illumination light using a digital color camera. This image is shown in FIG. 11B.

Figure 11C:
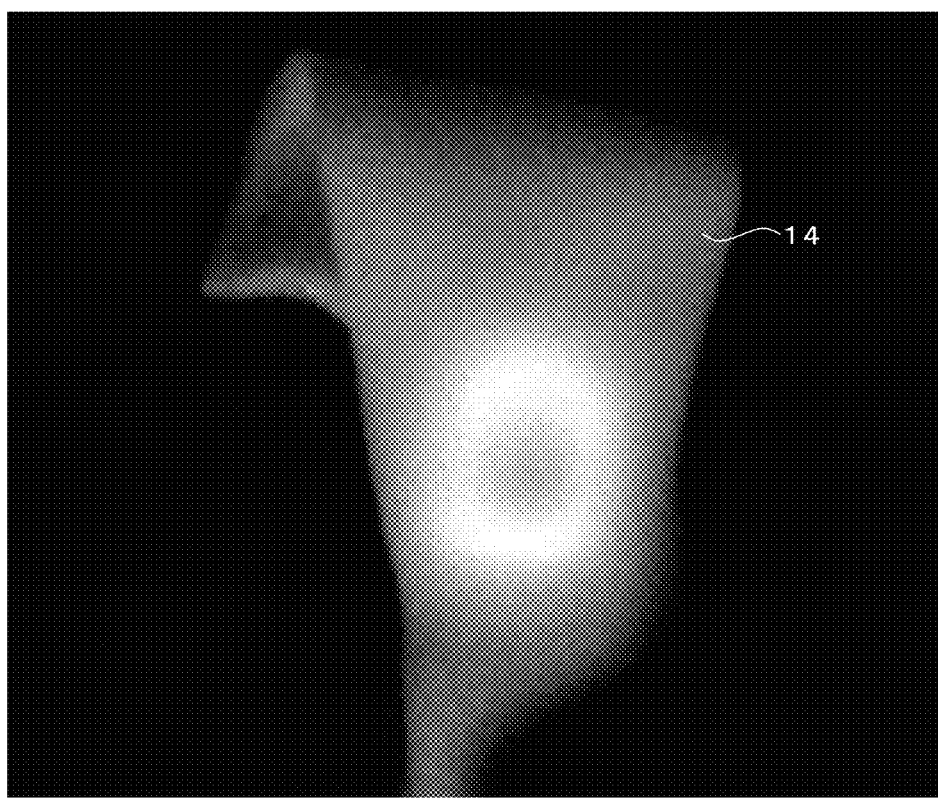
FIG. 11C is an image of the front surface of the silicone sheet behind which the medical tool for fingertip 1A of Example is placed, the front surface being irradiated with excitation light and imaged using a near-infrared color system.

Further, excitation light (wavelength of from 740 to 760 nm) was applied from the front surface of the silicone sheet 14 and an image of the front surface was captured by a near-infrared color camera system (MIZUHO Corp.). This image is shown in FIG. 11C. As shown in FIG. 11C, a dark part corresponding to the opening portion 2 could be observed inside the light-emitting part having a finger cot shape. This demonstrates that the position of the affected site can be specified from the serosal side by pressing down the affected site on the mucosal side of the body cavity by the ball of the finger exposed from the opening portion 2 of the medical tool for fingertip 1A, followed by application of the excitation light.

REFERENCE SIGNS LIST 1 medical tool main body
1A, 1B, 1C, 1D, 1E, 1F, 1G, 1H, 1I medical tool for fingertip
2 opening portion
3 pull string
3a attachment region of pull string
4 scales
5 holes punched out in a shape of scales
6 red or near-infrared light nontransmitting resin film
7 glove
8 printing layer or resin layer having ring shape
9 circular printing layer
10 resin layer having ring shape and adhesive layer provided to one surface
11 release film
12 surgical glove
13 circular resin layer having adhesive layer provided to one surface 14 silicone sheet
15 resin without fluorescence dye
h1 length
w1 width

The invention claimed is:

1. A medical tool which is used by putting it on a fingertip, wherein the medical tool has a finger cot shape and an opening portion from which a ball of a finger is exposed when the medical tool is put on the finger, and the medical tool is formed of a resin that emits red fluorescence or near-infrared fluorescence.

2. The medical tool according to claim 1, wherein the medical tool has a length so that the medical tool covers the finger from the fingertip to a second joint of the finger when the medical tool is put on the finger, the medical tool being provided with scales from the opening portion to a finger insertion side, the scales being formed of a red or near-infrared light nontransmitting resin.

3. The medical tool according to claim 2, wherein a pull string is attached.

4. The medical tool according to claim 1, having a length so that the medical tool covers the finger from the fingertip to a second joint of the finger when the medical tool is put on the finger, the medical tool having a red or near-infrared light nontransmitting resin layer from the opening portion to a finger insertion side, wherein the red or near-infrared light nontransmitting resin layer has holes from which the resin that emits red fluorescence or near-infrared fluorescence is exposed, and the holes are formed in a shape of scales.

5. The medical tool according to claim 4, wherein a pull string is attached.

6. The medical tool according to claim 1, having the resin that emits red fluorescence or near-infrared fluorescence around the opening portion.

7. The medical tool according to claim 1, wherein a pull string is attached.

8. A medical tool for palpation, wherein the medical tool has a glove shape and a resin layer on or around a ball of a finger thereof, wherein the resin layer emits red fluorescence or near-infrared fluorescence.

9. A medical tool for palpation which is used by putting it on a fingertip,
wherein the medical tool is a sticker-like medical tool having a resin layer and an adhesive layer provided to one surface of the resin layer, and the resin layer emits red fluorescence or near-infrared fluorescence, and
wherein the medical tool has a size that allows it to be attached to a ball of a finger and an opening portion with a width of from 5 to 15 mm and a length of from 5 to 20 mm that forms a ring shape.

10. The medical tool according to claim 9, wherein the resin layer as a part to be placed on the finger has a thickness of from 0.1 to 0.3 mm.

11. A medical tool for palpation, which is used by putting it on a fingertip,
wherein the medical tool is a sticker-like medical tool having a resin layer and an adhesive layer provided to one surface of the resin layer and the resin layer emits red fluorescence or near-infrared fluorescence,
wherein the medical tool has a size that allows it to be attached to a ball of a finger and an opening portion that has a size enabling palpation, and
wherein the resin layer has a thickness of from 0.1 to 0.3 mm, a tensile force at break of 9.0 N or more, an elongation at break of 600% or more, and a tensile force at 300% elongation of 3.0 N or less according to JIS T9107 so as to be as thin and flexible as a surgical glove.

* * * * *